US00PP15956P2

(12) United States Plant Patent
Olesen et al.

(10) Patent No.: US PP15,956 P2
(45) Date of Patent: Sep. 13, 2005

(54) CLIMBING ROSE PLANT NAMED 'POULYC005'

(50) Latin Name: *Rosa hybrida*
Varietal Denomination: POULyc005

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 96 days.

(21) Appl. No.: 10/719,712

(22) Filed: Nov. 21, 2003

(51) Int. Cl.[7] ..... A01H 5/00
(52) U.S. Cl. ..... Plt./114
(58) Field of Search ..... Plt./109, 112, 113, Plt./114

(56) References Cited

U.S. PATENT DOCUMENTS

PP9,288 P * 9/1995 DeVor ..... Plt./114

OTHER PUBLICATIONS

UPOV ROM GTITM Computer Database, GTI Jouve Retrieval Software 2004/04 Citation for 'POULC005'.*

* cited by examiner

*Primary Examiner*—Kent Bell
*Assistant Examiner*—W. C. Haas

(57) ABSTRACT

A new climbing garden rose plant which has abundant, light pink and orange blend flowers and attractive foliage. This new and distinct variety has shown to be uniform and stable in the resulting generations from asexual propagation.

1 Drawing Sheet

Botanical classification: *Rosa hybrida.*
Variety denomination: 'POULyc005'.

The present invention constitutes a new and distinct variety of garden rose plant which originated from a controlled crossing between a female parent 'POULsint', (unpatented), and the male parent, an unnamed plant. The two parents were crossed during the summer of 1994, and the resulting seeds were planted in a controlled environment in Fredensborg, Denmark. The new variety was selected as a single plant from the controlled cross and is named 'POULyc005'.

The new variety may be distinguished from its female parent, 'POULsint', by the following combination of characteristics:

1. The female parent has very small flower size, less than 5 cm while 'POULcy005' has a flower size of 25–40 mm when open.
2. The female parent has narrow and bushy growth habit while 'POULyc005' has a broader climbing growth habit.

The new variety may be distinguished from its male parent, an unnamed plant, by the following combination of characteristics:

1. The male parent flower petal color, open flower, upper surface is White Group 155D. 'POULyc005' flower petal color, open flower, upper surface is Orange Group 27C with intonations of White Group 155B at basal zone.
2. The male parent has a wild rose scent; however, 'POULyc005' has a light floral scent.

The objective of the hybridization of this rose variety was to create a new and distinct variety for garden use with unique qualities, such as:

1. Uniform and abundant light pink flowers.
2. Vigorous, but compact growth when propagated both as a budded rose and on its own roots.

3. Disease resistance.
4. Improved flowering habit. Since the variety is less apically dominant than what is typical of climbing roses, flowers are produced evenly from the lower branches to the top.

This combination of qualities is not present in previously available commercial cultivars of this type, known to the inventor, and distinguishes 'POULyc005' from all other varieties of which we are aware.

As part of their rose development program, L. Pernille Olesen and Mogens N. Olesen germinated the seeds from the aforementioned hybridization during winter 1994 and conducted evaluations on the resulting seedlings in a controlled environment in Fredensborg, Denmark.

'POULyc005' was selected in the spring 1995 by the inventors as a single plant from the progeny of the aforementioned hybridization.

Asexual reproduction of 'POULyc005' by traditional budding and rooted cuttings was first done by L. Pernille and Mogens N. Olesen in their nursery in Fredensborg, Denmark in July, 1995. This initial and other subsequent asexual propagations conducted in controlled environments have demonstrated that the characteristics of 'POULyc005' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULyc005'. Specifically illustrated in THE DRAWING:

FIG. 1.1; Open flower and stem showing open flowers, the attachment of buds, and peduncles;

FIG. 1.2; Flower buds closed and partially open.

FIG. 1.3; Flower petals, detached;

FIG. 1.4; Sepals, receptacle, and pedicel;

FIG. 1.5; Mature leafs and juvenile leaf;

FIG. 1.6; Bare stem with thorns.

DETAILED DESCRIPTION OF THE VARIETY

The following is a description of 'POULyc005', as observed in its growth in typical outdoor conditions in a field nursery in Jackson County, Oreg. Observed plants are 3 years of age. Color references are made using The Royal Horticultural Society (London, England) Colour Chart, 1995, except where common terms of color are used.

For a comparison, several physical characteristics of the rose variety 'POULover' (U.S. Plant patent application Ser. No. 10/341,890) are compared to 'POULyc005' in Chart 1.

CHART 1

| | 'POULyc005' | 'POULover' |
|---|---|---|
| Bud color as sepals unfold | Petals are Orange Group 27A; at ¼ opening, petals are Red Group 36A. | Petals are Red Group 55C; at ¼ opening, petals are Red Group 55C. |
| Receptacle Color | Green Group 143C. | Yellow-Green Group 144A. |
| Outermost Petals upon opening, outer side | Red Group 36B at petals margins. White Group 155B at basal zone. | Red-Purple Group 65A at petal margins. Red-Purple 65D at mid petal. |

Parents:

*Seed parent.*—POULsint.

*Pollen parent.*—Un-named Plant.

FLOWER AND FLOWER BUD

Blooming habit: Continuous.

Flower bud:

*Size.*—Upon opening, 18 mm in length from base of receptacle to end of bud. Bud diameter is normally 12 mm.

*Bud form.*—Short and pointed ovoid.

*Bud color.*—As sepals unfold, petals are Orange Group 27A. Red Group 36A at ¼ opening. Sepals: Sepal Shape: Apex: Cirrhose. Base: Flat at the union with the receptacle. Sepal Size: 15 to 18 mm long by 5 to 7 mm wide. Upper Surface: Color: Green Group 137B. Texture: Moderately Pubescent. Lower Surface: Color: Yellow-Green Group 146B. Shape: Margins have strong foliaceous appendages on three of the five sepals. Stipitate glands are few in quantity. Size: 21 mm long by 9 mm wide.

*Receptacle.*—Surface Texture: Smooth and glabrous. Shape: Urn-shaped. Size: 5 mm (h)×5 mm (w). Color: Green Group 143C.

*Peduncle.*—Surface: Smooth and glabrous with few stipitate glands. Length: 15 to 20 mm average length. Diameter: 2 mm (average). Color: Yellow-Green Group 144C. Strength: Weak.

*Borne.*—Multiples of 9 buds per flowering stem on average.

Flower bloom:

*Fragrance.*—Light floral.

*Duration.*—The blooms have a duration on the plant of approximately 7 to 10 days. Petals drop away cleanly from the receptacle after flowers have fully matured.

*Size.*—Average flower diameter is 25–40 mm when open. Flower depth is normally 15 to 18 mm.

*Form.*—Spray. Individual flowers are rosettes with strong petal overlap.

*Shape of flower when viewed from the side.*—Upon opening, upper part: Flat. Upon opening, lower part: Concave. Open flower, upper part: Flattened convex. Open flower, lower part: Concave.

*Petalage.*—Double. Average range: 30–35 petals under normal conditions with 8 petaloids.

Color:

*Upon opening, petals.*—Outermost petals: Outer side: Red Group 36B with intonations of White Group 155B at basal zone. Inner side: Red Group 36B with intonations of White Group 155B at basal zone. Innermost petals: Outer side: Orange Group 29D to Red Group 36D with intonations of White Group 155B at basal zone. Inner side: Orange Group 29D to Red Group 36D with intonations of White Group 155B at basal zone.

*Upon opening, basal petal spots.*—Outermost petals: Outer side: None. Inner side: None. Innermost petals: Outer side: Yellow Group 11C to 11D. Inner side: Yellow Group 11C to 11D.

*After opening, petals.*—Outermost petals: Outer side: Orange Group 27C with White Group 155B at basal zone. Inner side: Orange Group 27C with White Group 155B at basal zone. Innermost petals: Outer side: Orange Group 27C with White Group 155B at basal zone. Inner side: Orange Group 27C with White Group 155B at basal zone.

*After opening, basal petal spots.*—No distinctive coloration at petal base observed.

General tonality: On open flower Orange Group 29C to 29D. No change in the general tonality at the end of the $10^{th}$ day.

*Petals.*—Petal Reflex: Petals reflex very slightly. Margin: Entire with point in center of margin. Shape: Apex: Round. Base: Varying from acute to rounded. Size: 16–19 mm (l)×13–21 mm (w). Texture: Smooth. Thickness: Thin. Arrangement: Not Formal.

*Petaloids.*—Quantity: 6–8. Color: Upper surface: Orange Group 27C. Lower surface: Orange Group 27C. Size: Typically 15 mm in length by 5 mm wide. Shape: Elliptic and irregular. Apex: Rounded. Base: Acute.

Reproductive organs:

*Pistils.*—Length: 4 mm long. Quantity: 38 (actual count).

*Pollen.*—None observed.

*Anthers.*—Color: Yellow-Orange Group 18B with margins Yellow-Orange Group 16A. Quantity: 57 (actual count).

*Filaments.*—Color: Yellow Group 8C. Length: 4–5 mm.

*Stigmas.*—Slightly inferior in location to anthers. Color: Yellow-Green Group 150D.

*Styles.*—Color: Yellow-Green Group 145C.

*Hips.*—None Observed in the field nursery in Jackson County Oreg.

PLANT

Plant growth: Vigorous, very tall climbing habit of 150–200 cm in height. Since plant is less apically dominant flowering occurs evenly from lower branches to the top.

Stems:

*Color.*—Young wood: Yellow-Green Group 144B. Older wood: Yellow-Green Group 144B.

*Surface texture.*—Young wood: Smooth. Older wood: Smooth.

*Thorns.*—Incidence: 10 thorns per 10 cm of stem. Size: Average length: 4 mm. Color: A blend of Greyed-Orange Group 174C and Greyed-Red Group 181A. Shape: Linear to concave.

*Anthocyanin.*—None observed.

Plant foliage: Normal number of leaflets on normal leaves in middle of the stem: 7 leaflets.

*Compound leaf size.*—70–57 mm (l)×30–35 mm (w).

*Color.*—Mature Foliage: Upper Leaf Surface: Yellow-Green Group 146A. Lower Leaf Surface: Yellow-Green Group 147C. Juvenile foliage: Upper Leaf Surface: Yellow-Green Group 146A. Lower Leaf Surface: Yellow-Green Group 147C. Anthocyanin: None observed.

Plant leaves and leaflets:

*Stipules.*—Size: 20–24 mm. Quantity: 2 per compound leaf. Color: Yellow-Green Group 144A. Margins: Finely serrated with moderate to few stipitate glands. Shape: Linear with outward extending apices.

*Petiole.*—Length: 25 to 30 mm. Diameter: 2 mm. Color: Yellow-Green Group 144B with prickles underneath. Anthocyanin: None Observed.

*Rachis.*—Color: Yellow-Green Group 144B with prickles underneath. Anthocyanin: None Observed. Length: 20 mm.

*Leaflet.*—Edge: Finely serrated. Shape: Generally ovate. Apex: Cuspidate. Base: Rounded. Texture: Smooth. Arrangement: Odd pinnate. Venation: Reticulate. Glossiness: Moderately Glossy. Size: 23 mm (l)×18 mm (w).

Disease resistance: Above average resistance to mildew, rust, black spot, and *Botrytis* under normal growing conditions in Jackson County, Oreg.

Cold hardiness: The variety 'POULyc005' has been found to be cold tolerant to USDA Cold Hardiness Zone 6.

We claim:

1. A new and distinct variety of rose plant of the climbing rose class, substantially as herein illustrated and described as a distinct and novel rose variety due to its abundant light pink and orange blend flowers, disease resistance, and extended period of bloom.

* * * * *

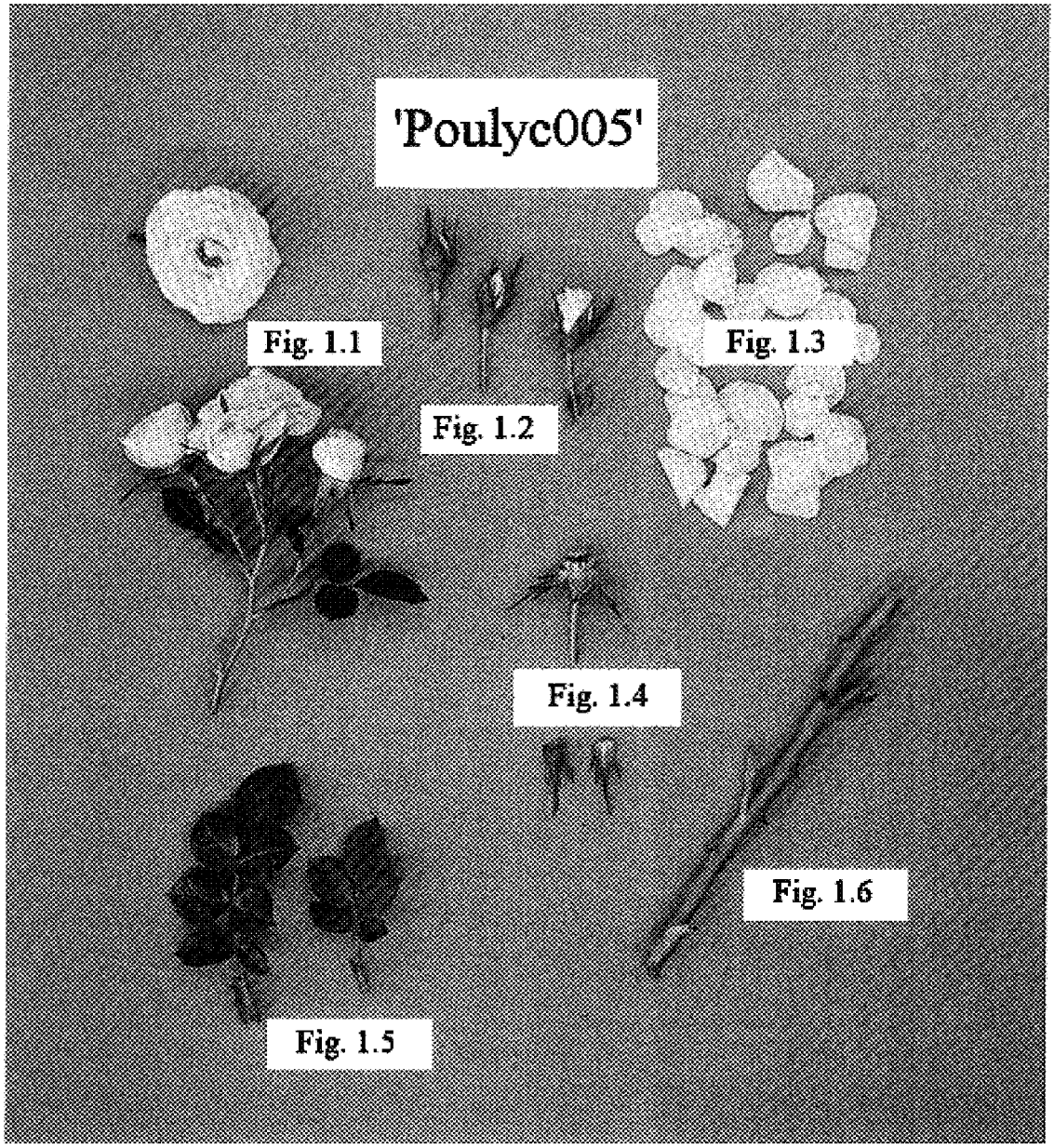
'Poulyc005'
Fig. 1.1
Fig. 1.2
Fig. 1.3
Fig. 1.4
Fig. 1.5
Fig. 1.6